United States Patent [19]
Greener

[11] Patent Number: 6,017,748
[45] Date of Patent: *Jan. 25, 2000

[54] CLONING HOST ORGANISMS

[75] Inventor: Alan L. Greener, Del Mar, Calif.

[73] Assignee: Stratagene, La Jolla, Calif.

[*] Notice: This patent is subject to a terminal disclaimer.

[21] Appl. No.: 08/488,423

[22] Filed: Jun. 7, 1995

Related U.S. Application Data

[63] Continuation of application No. 08/441,368, May 15, 1995, Pat. No. 5,552,314, which is a continuation of application No. 08/051,572, Apr. 22, 1993, abandoned, which is a continuation of application No. 07/462,505, Jan. 8, 1990, abandoned.

[51] Int. Cl.$^7$ .............................. C12N 1/20; C12N 15/00; C12N 1/00; C07H 21/02

[52] U.S. Cl. ................................. 435/252.33; 435/320.1; 435/243; 536/23.1

[58] Field of Search ........................... 435/252.3, 252.33, 435/320.1, 172.3, 91.4, 91.42, 848, 849; 536/23.1, 23.2, 23.4, 23.5, 23.51, 23.52, 23.53, 23.6, 23.7, 23.71, 23.72, 23.74, 24.1, 24.2, 24.3, 24.31, 24.32, 24.23; 935/9, 10, 23, 29, 59, 66, 72, 73, 80

[56] References Cited

U.S. PATENT DOCUMENTS

| | | | |
|---|---|---|---|
| 5,512,468 | 4/1996 | Greener | 435/172.3 |
| 5,552,314 | 9/1996 | Greener | 435/252.3 |

OTHER PUBLICATIONS

Kolodner et al. 1985 J. Bacteriol. 163(3): 1060–1066.
Ishiura et al. 1989 J. Bacteriol. 171(2): 1068–1074.
Bullock et al. 1987 Bio Techniques 5(4): 376–379.
Raleigh et al. 1986 Proc. Natl. Acad. Sci., USA 83: 9070–9074.
Heitman et al. 1987 J. Bacteriol. 169(7): 3243–3250.
Chalker et al. 1988 Gene 71: 201–205.
Bachmann 1983 Microbiol. Rev. 47(2): 180–230.
Watson et al. 1987 in: Molecular Biology Of The Gene, fourth edition, Benjamin/Cummings Publishing Company, Menlo Park, CA, p. 313.

*Primary Examiner*—Bruce R. Campell
*Assistant Examiner*—Shin-Lin Chen
*Attorney, Agent, or Firm*—Finnegan, Henderson, Farabow, Garrett & Dunner, L.L.P.

[57] ABSTRACT

Methods and materials for the cloning of DNA, in particular, for the cloning of "unclonable" DNA using genetically engineered host cells. Host cell organisms have been discovered that stabilize and inhibit rearrangement of DNA molecules capable of forming non-standard secondary and tertiary structures. organisms are engineered to contain at least one mutation which inactivates homologous recombination and at least one mutation in a DNA repair pathway. Examples of such DNA pathways include UV repair pathway, the SOS repair pathway, the mismatch repair pathway, the adaptive response pathway, the heat shock response pathway, the osmotic shock response pathway, the repair pathway of alkylation damage, the repair pathway of uracil incorporation into DNA and pathways involved in maintaining DNA superhelicity. The host organisms of this invention are suitable for cloning DNA capable of forming non-standard and tertiary structures such as found in eukaryotic DNA.

24 Claims, 4 Drawing Sheets

RECOMBINATION PATHWAYS IN E. COLI

ALL PATHWAYS REQUIRE
$recA^+$

↓

| RecBDC | RecE | RecF |
|---|---|---|
| $recB^+$ | $recE^+(sbcA^-)$ | $sbcBC^-$ |
| $recC^+$ | $recF^+$ | $recF^+$ |
| $recD^+$ | $recJ^+$ | $recJ^+$ |
|  | $recO^+$ | $recN^+$ |
|  |  | $recO^+$ |
|  |  | $recQ^+$ |
|  |  | $ruv^+$ |

FIG. 1

CLONING HOST ORGANISMS

This is a continuation of application Ser. No. 08/441,368, filed May 15, 1995 U.S. Pat. No. 5,552,314, which is a continuation application of Ser. No. 08/051,572, filed Apr. 22, 1993, abandoned, which is a continuation of application Ser. No. 07/462,505 filed Jan. 8, 1990, abandoned.

BACKGROUND

1. Field of the Invention

This invention relates to certain methods and materials for the cloning of DNA and, in particular, to the cloning of "unclonable" DNA using a genetically engineered host cell. This cloning host organism includes particular mutations from existing cells which have been found to stabilize tester DNA plasmids, and can be assembled using standard transducing and plating techniques.

2. Description of Related Art and Introduction to the Invention

The ability to elucidate gene structure and function often depends to a great extent upon the construction of recombinant DNA libraries accurately representing the total genome of a subject organism, followed by the cloning of this recombinant DNA. Generally, the total DNA of cells from the subject organism is isolated and cut into fragments using specific restriction enzymes. The fragmented DNA sequences are then inserted into appropriate vectors for subsequent propagation and amplification in a foreign host. Commonly used vectors include plasmids, cosmids or phages. Examples of host cells suitable for propagation of foreign DNA sequences include bacteria (i.e., *E. coli Bacillus sabtilis, Pseudomonas aeruginosa*, yeast (i.e., *Saccharomyces cerevisiae*) Drosophilia (i.e., *Drosophilia melongaster*) mammalian cell lines (CHO, L-cells) human cell lines (i.e., Hela, Baculovirus, plant cell lines.

To date a number of obstacles have limited the establishment or stable inheritance of foreign (non-native) DNA in host cells. One barrier to establishment of foreign DNA is the presence of restriction endonuclease that cleave such DNA. See, e.g., Bickle, T. (1982) In: *Nucleases* (Linn, S. M., and Roberts, R. J., eds.). Cold Spring Harbor Press, Cold Spring Harbor, N.Y.; Raleigh, E. A., and Wilson, G. (1986) *Proc. Natl. Acad. Sci. USA* 83:9070; and Heitman, J., and Model, P. (1987) *J. Bact.* 169:3243. Genetic inactivation of these restriction enzymes in certain host cells (restriction minus strains) can result in a more efficient introduction of foreign DNA via transformation, transduction, electroporation or conjugation.

Despite such genetic manipulation of host cells, however, many DNA fragments, particularly those from eucaryotic organisms, have been deemed "unclonable." Many of these "unclonable" DNA segments are known to contain sequences capable of forming non-standard secondary and tertiary structures. See, e.g., Erlich, D. (1989) In: *Mobile DNA* (Berg, D. E. and Howe, M. M., eds.). ASM Publications, Washington D.C. and Santella, R. M., Grunberger, D., Weinstein, I. B., and Rich, A. (1981) *Proc. Natl. Acad. Sci. USA* 78:1451. DNA that is capable of forming cruciforms (hydrogen bonded hairpin structures formed from inverted repeat sequences) and Z-DNA (a left handed zig zag configured DNA resulting from alternating purine-pyrimidine residues), for example, is rapidly deleted or rearranged in *E. coli*. See, e.g., Santella, R. M., Grunberger, D., Weinstein, I.B., and Rich, A. (1981) *Proc. Natl. Acad. Sci. USA* 78:1451 and Fuchs, R. P. P., Freund, A. M., and Bichara, M. (1988) In: Methods and Consequences of DNA Damage Processing (Friedberg, E. C. and Hanawalt, P. C., eds.). Alan R. Liss, Inc., New York.

Previous attempts to increase the stability of cloning such complex DNA structures has met with only limited success. See Wyman, A., Wertman, K., Barker, D., Helms, C., and Petri, W. (1986) Gene 49:263–271. Wyman et al. reported that certain mutations in *E. coli* host cells resulted in an increased fidelity of representation of certain complex eucaryotic DNA sequences. Specifically, this group found that the use of *E. coli* strains with mutations in homologous recombination pathways (recB, recC, and sbcB, or recD) increased the representation of polymorphic sequences of genomic DNA. While these authors did not fully characterize the polymorphic nature of the DNA sequences cloned, the subject sequences were thought to contain long segments of inverted repetitions or palindromes.

Chalker et al. have reported that the mutation of a single *E. coli* gene involved in a secondary pathway of homologous recombinations (sbcC) results in the stable propagation of a long palindromic DNA sequence. Chalker, A., Leach, D., and Lloyd, R. (1988) *Gene* 71:201–205. In marked contrast to the study of Wyman et al., however, the Chalker group did not observe any major effects of mutations in the primary pathway of homologous recombination on palindrome stability. Ishiura et al. studied the effects of mutant strains of *E. coli* on the deletion of genomic eucaryotic DNA during cloning. Ishiura, M., Hazumi, N., Koide, T., Uchida, T., and Okada, Y. (1989) *J. Bact.* 171:1068–1074. These authors report that only a quadruple combination of host mutations (recB, recc, sbcB and either recJ or recN) prevented the deletion of DNA segments during host propagation. Strains with single mutations in either primary or secondary pathways of homologous recombination or combined mutations in recombination and restriction pathways did not prevent deletion. There were no data on the structural configuration of the DNA sequences employed.

The data from these studies, taken together, indicate that host cell mutations of recombination pathways have not lead to increased stability of certain forms of complex DNA during propagation, and the divergent and often conflicting results noted above indicate that, at present, there is not an identifiable or even ascertainable host strain that is suitable for cloning complex, eucaryotic DNA.

The present inventor has discovered that complex DNA sequences can be stabilized during cloning by utilizing hosts with combined mutations in certain nucleic acid recombination and repair pathways. Described herein are novel bacterial hosts designed for cloning foreign DNA by combining DNA repair mutations into host strains deficient in homologous recombination. Mutations which allow for stabilization of tester plasmids containing complex DNA are identified in existing strains and then assembled using standard techniques of transduction, screening, selection and propagation. The resulting bacteria can be used to stabilize and clone complex DNA such as contained in eucaryotic genomes.

SUMMARY OF THE INVENTION

This invention provides for the genetic construction of host organisms that provide a stable environment for cloning foreign DNA molecules capable of assuming secondary and tertiary structure susceptible of rearrangement. These hosts are, thus, suitable for cloning DNA molecules capable of assuming such secondary and tertiary structures. The host organisms of this invention provide a stable environment for DNA molecules containing inverted repeat sequences, capable of forming cruciforms, and DNA molecules containing alternating purine-pyrimidine residues, capable of forming Z-DNA. The host organisms of the invention are characterized as being recombination deficient and containing genetic mutations in DNA repair pathways. In a preferred embodiment, this invention provides for an *E. coli* host of the genotype recB, recJ, sbcC201, phoR, uvrC, umuC::Tn5, mcrA, mcrB, mrr, Δ(hsdRMS), endA1, gyrA96, thi, relA1, lac*, supE44, {F'proAB, lacI$^Q$ZΔM15::Tn10}.

The invention further provides for a method of cloning structurally complex DNA, such as found in the eucaryotic genome. This method comprises isolating DNA from an organism, cutting the DNA into fragments, inserting DNA fragments of that organism into a vector, and introducing the vector in the insert into the host organism of this invention. The method involves the use of a host characterized as recombination deficient with mutations in DNA repair systems. In a preferred embodiment, the *E. coli* host used in cloning is of the genotype recB, recJ, sbcC201, phoR, uvrC, umuC::Tn5, mcrA, mcrB, mrr, Δ(hsdRMS), endA1, gyrA96, thi, relA1, lac*, supE44, {F'proAB, lacI$^Q$ZΔM15::Tn10}.

This invention further provides for a method of constructing a host organism suitable for cloning DNA molecules capable of assuming secondary and tertiary structures susceptible of rearrangement. The method comprises identifying mutations of recombination and DNA repair pathways which stabilize DNA in existing hosts and assembling these mutations using standard genetic techniques. This invention further provides for construction of a novel strain of *E. coli*, designated SURE™ Construction of the SURE™ strain is accomplished by successively transducing *E. coli* ER1451 with bacterial genomes containing mutations in recombination and DNA repair systems. A preferred method of constructing the SURE™ strain is outlined in FIG. 2 and further described herein.

BRIEF DESCRIPTION OF THE DRAWINGS

FIG. 1 is a schematic representation of the recombination pathways of *E. coli*.

DETAILED DESCRIPTION OF THE INVENTION

Figure 2:
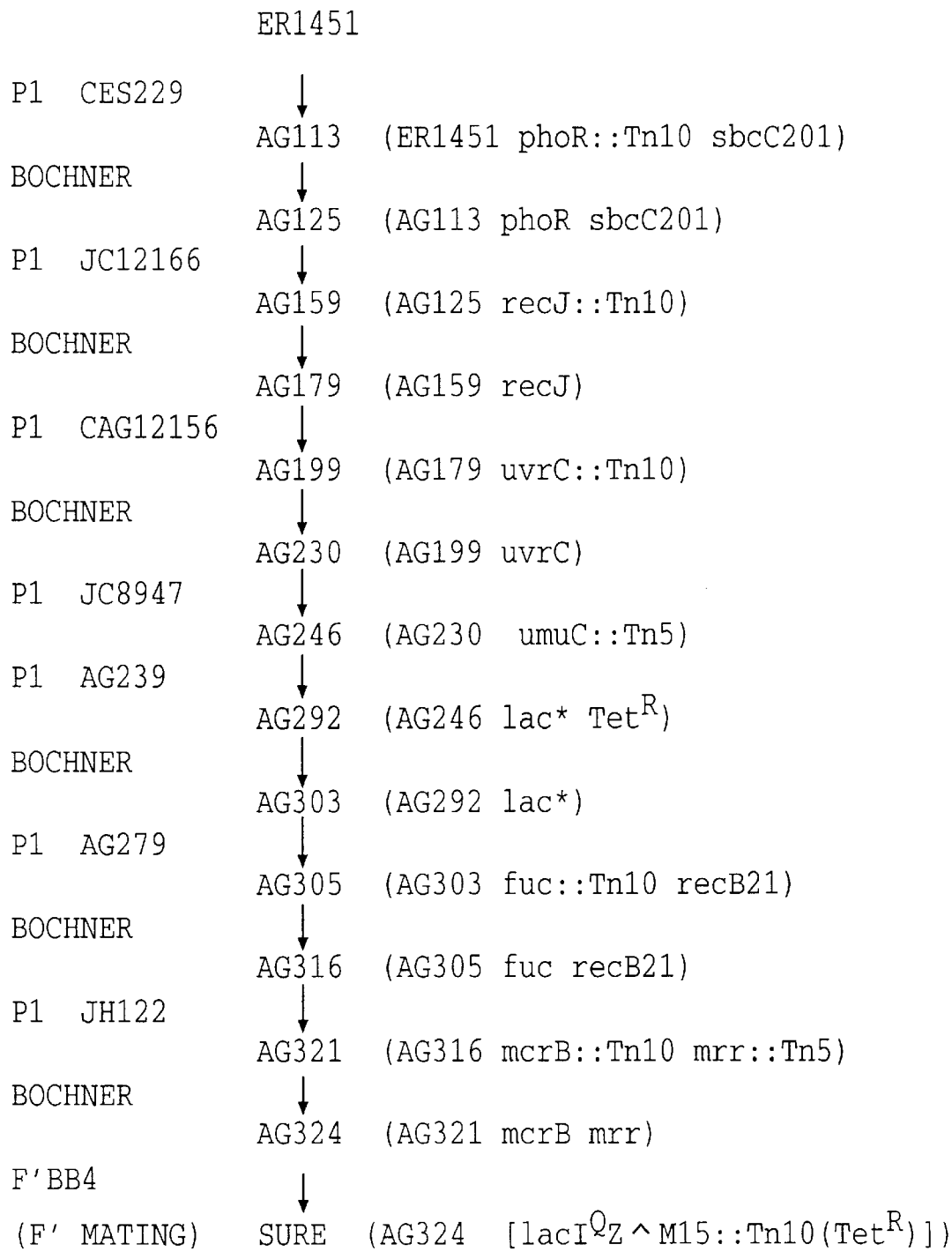
FIG. 2 is a flow diagram of the steps used to construct a strain of *E. coli* that is suitable for cloning DNA capable of forming secondary and tertiary structures susceptible of rearrangement. The SURE™ strain was assembled from ER1451 using sequential steps of P1 transduction (P1) Bochner plating, and conjugal mating. The *E. coli* strain designation for each P1 transduction step indicates the source of genetic material transduced. The genotypes of these strains are set forth in Table 1.

I. Abbreviation—the following abbreviations are used throughout the specification and claims.

A. Relevant Genotypes end—endonuclease hsd—host specificity restriction system mcr—restriction system for DNA containing methylated cytosine residues mrr—restriction system for DNA containing methylated adenine residues recBC—Exonuclease V. involved in primary homologous recombination pathway sbcC—suppressor of recBC thr—threonine umuC—uv mutagenesis uvr—ultraviolet repair (excision repair system)

recJ—exonuclease involved in secondary homologus recombination pathways lac*—an uncharacterized mutation within the lac operon which results in colonies more intensely blue in the presence of the lacZ ΔM15 mutation and a source of the α-complementation lac segment B. Other DNA—deoxyribonucleic acid

*E. coli*—*Escherichia coli* bacteria

SOS—genes coding for components of DNA repair systems; inducible by DNA damage

II. Definitions—Unless otherwise indicated, the terms listed below will be defined as set forth.

cruciform—hydrogen bonded hairpin structures formed from inverted repeat sequences of DNA infection—any process used to introduce DNA into host organisms. Includes transduction, transformation transtection, conjugal mating, and electroporation.

insertion—any process used to integrate foreign DNA into vectors inverted repeats—completely or partially identical but oppositely oriented DNA sequences restriction minus—cell strains lacking genes coding for enzymes which break down foreign DNA vector—autonomously replicating DNA units into which DNA fragments are inserted for cloning Z-DNA—a left-handed helical configuration of DNA resulting from alternating purine-pyrimidine residues Construction of mutant bacterial strain DNA molecules, capable of assuming nonstandard secondary and tertiary structures, and as commonly found in eucaryotic genomes, are often completely deleted or rearranged during propagation in cloning host cells. A major reason for this lack of fidelity in cloning may be the existence in the host cell of mechanisms related to the replication and repair of DNA. Examples of such mechanisms include: (1) pathways designed for homologous or non-homologous recombination; (2) restriction systems which cleave foreign DNA sequences; (3) endonucleases which catalyze the breakdown of DNA; and (4) systems designed for repair of DNA. Both procaryotic and eucaryotic organisms have developed an extensive array of systems designed for DNA repair. Examples of such repair systems include: uv repair pathway; SOS repair pathway; mismatch repair; adaptive response; heat shock response; osmotic shock response; repair of alkylation damage; repair of uracil incorporation into DNA; and gene products involved in maintaining DNA superhelicity. The role of such repair systems in cloning of foreign DNA has not yet been investigated. As noted above, prior attempts to increase stabilization of foreign DNA have focused only on host cell mutations in the recombination and/or restriction pathways.

The inventors have engineered a host organism with mutations in repair as well as recombination pathways. The resulting host cells serve to stabilize various complex forms of DNA during propagation.

The new strain has been designed to be a superior host for optimizing the construction of cDNA and genomic DNA libraries as well as for increasing the probability that the individual clones obtained will accurately reflect the genetic makeup of the subject organism. The construction of host strains with combined mutations was accomplished by crossing or mating strains with individual mutations in metabolic pathways. Means of constructing new strains by DNA introduction or mutation include, but are not limited to, Hfr mating, generalized transduction, specialized transduction, conjugation, transposon mutagenesis, oligonucleotide-directed mutagenesis, and transformation followed by genetic recombination. Examples of transducing bacteriophages include, but are not limited to, P1 or lambda. Details of a preferred method of construction using P1 phage transduction are presented in Example 1. Screening and identification of mutant strains incorporating and expressing the transduced foreign DNA can be accomplished by any number of methods. Examples of such identification and screening methods include, but are not limited to, screening for phenotypic traits such as antibiotic sensitivity, drug resistance, or dependency on nutrient sources.

The parent strain, used as the basis for construction, can be any existing strain with a well-defined genotype that preferably includes at least one of the specific mutations sought to be present in the final genotype. Numerous such strains are available and have been well characterized. See, e.g., Ishiura, M., Hazumi, N., Koide, T., Uchida, T., and Okada, Y. (1989) *J. Bact.* 171:1068–1074. The parent strain is then transduced with or mated with DNA from a second strain known to contain at least one additional desired mutation. Those progeny cells containing the desired mutations from both the donor and recipient cell are identified, propagated and used through subsequent transduction or mating steps. Once the organism is identified which contains all of the desired mutations, such an organism can be additionally manipulated to make it suitable with a variety of vectors and screening procedures. The invention is a propagatable cell containing combined mutations in both recombination and DNA repair systems. Preferably, the cloning host cell also contains mutations in the endonuclease and restriction systems, which mutations increase the utility of host cells for cloning purposes.

In a preferred embodiment, the inventors have engineered and constructed a novel strain of *E. coli*, with combined mutations in recombination and repair systems, that stabilizes complex foreign DNA during propagation. *E. coli* strain ER1451, known to have mutations of certain DNA endonucleases and components of the restriction pathway, was sequentially transduced with bacterial genomes having the mutations sought to be introduced. In each case, the transduced DNA also contained a gene for tetracycline resistance. Following each individual transduction step, strains containing the combined mutations were screened on Bochner plates in order to isolate tetracycline sensitive derivatives which would then serve as a recipient for the next transduction step. Successive transduction steps can be performed in any order. In a preferred embodiment, the ER1451 strain was transduced sequentially with DNA containing mutations in the recombination pathway, ultraviolet repair pathway, SOS repair pathway, the restriction pathway, a tetracycline-resistant F'episome carrying a blue/white screening cassette and a lactose sensitivity gene. As a result of these sequential transduction and screening procedures, a strain of bacteria was created that is recombination deficient, restriction minus, endonuclease deficient, and with mutations in DNA repair systems. Details of this preferred construction sequence are given in Example 1. The resulting bacterial host, constructed by this method, is known as SURE, a trademark of Stratagene Cloning Systems.

The SURE™ strain constructed by this method was then tested to determine its effect on the stability of cloned DNA sequences capable of forming secondary and tertiary structures and susceptible to rearrangement during propagation. Examples of such DNA sequences include, but are not limited to inverted repeats and alternating purine-pyrimidine residues.

Initial studies were performed to evaluate the effects of the SURE™ strain on the stability of inverted repeat DNA sequences, capable of forming structures known as cruciforms. An inverted repeat plasmid tester system was created by modifying plasmid pBR322. This tester plasmid system, designated pAL28α, used chloramphenicol resistance as the inverted repeat sequence. A variety of strains of *E. coli*, existing strains as well as the SURE™ strain, were infected with a tester inverted repeat plasmid. Inverted repeats were found to be rapidly rearranged in virtually all existing strains tested. In contrast to the results with existing strains, however, the SURE™ strain was found to provide a stabilizing environment for these inverted repeat sequences. The percentage of rearrangement was decreased 20 fold in the SURE™ strain when compared to the other strains tested. The SURE™ strain was, therefore, engineered to carry mutations blocking pathways responsible for repairing DNA lesions. Preferred specific mutations for blocking these two key pathways are uvrC and umuC respectively, although mutations in other genes of this pathway or mutations in other repair pathways would give the desired effect. This presence of these mutations was demonstrated to result in a 10 to 20 fold increase in stability of DNA containing long inverted repeats.

Z-DNA tester plasmids were created as derivatives of plasmid pBR322. The pBR322 plasmid, containing sequences for tetracycline and penicillin resistance, was modified to include a Z-DNA segment in the promoter region for chloramphenicol resistance. The newly created tester plasmid system was designated pAL20Z. This tester DNA plasmid was infected into existing strains of *E. coli* as well as the newly constructed SURE™ strain. The Z-DNA containing segments were quickly deleted in the existing strains while, in the SURE™ strain, deletion was significantly and markedly reduced. These data demonstrate that a combination of mutations in recombination and repair pathways, such as engineered in the SURE™ strain, provide a stabilizing influence to DNA capable of forming nonstandard secondary and tertiary structures.

In *E. coli*, homologous recombination is a complex, multicomponent process that can proceed by three interdependent pathways (see FIG. 1). These 3 pathways, recBCD, recE and recF, all require the recA gene product and a set of accessory proteins. A standard recA host, therefore, is completely deficient in homologous recombination. Recombination in a recb strain (the recBCD pathway is the primary pathway in a wild type *E. coli*) is reduced to approximately 0.5%. The residual activity is due to the presence of the recE and recF alternate pathways which do not involve recB. A recB recJ double mutant, however, is virtually identical to a recA strain in its recombination deficiency; recJ is required for both alternate pathways. To model this, recombination can be blocked in host organisms with a variety of mutations. In addition to the ones set forth above, examples of such alternate mutations include recB, reco and recB, recJ, recN.

The inventors discovered that insertion of either the recA or recB mutations into a sbcC, recJ, umuC, uvrC strain, stabilized both Z-DNA and inverted repeats. The recB derivative was found to exhibit superior stabilization effects.

This discovery, that combined mutations in recombination and DNA repair pathways, stabilize complex DNA during propagation is significant.

The cloning host organism of the instant invention is restriction minus, preferably carrying, in E. coli, hsd, mcr and mrr mutations. The absence of mcr and mrr restriction activity increases the size and representation of libraries constructed with methylated or hemimethylated DNA. The absence of hsd activity increases the size and representation of libraries constructed from sequences containing EcoK recognition sequences. An end mutation (inactivating a DNA endonuclease) was observed to result in mproved quality of plasmid DNA minipreps.

In a preferred embodiment, the host cell of this invention also harbors a tetracycline-resistant F'episome carrying the lacI$^Q$ZΔM15 cassette making it suitable for blue/white screening on plates supplemented with X-gal and IPTG. The uncharacterized mutation present in XL1-Blue cells, which makes both plaques and colonies more intensely blue when a source of the α-complementation fragment is introduced, has been added. The cell is, thus, suitable for plasmid or phage libraries using a variety of vectors.

The following examples are set forth to assist in understanding the invention and should not, of course, be construed as specifically limiting the invention described and claimed herein. Such variation of the invention which would be within the purview of those in the art, including the substitution of all equivalents now known or later developed, are to be considered to fall within the scope of the invention as hereinafter claimed.

EXAMPLE 1
Construction of an E. coli strain.

A novel strain of E. coli was constructed from existing strains utilizing standard transduction and plating techniques. In this example, transduction with P1 phage particles was utilized. Bochner plating was then used to screen derivatives for the desired genotype. An outline of the construction method is schematically diagrammed in FIG. 2. The genotypes of the various E. coli strains used in the construction pathway are set forth in Table 1.

TABLE #1

Genotypes

| Strain | |
|---|---|
| ER1451 | Δ(lac-proAB), thi, gyrA96, endA1, hsdR17, relA1, supE44, {F' traD36, proAB, lacI$^Q$Z M15} |
| CES229 | recD1009, hsdR, sbcC201, phoR79::Tn10, recA |
| JC12166 | recB21, recC22, sbcB15, sbcC201, thr-1, leuB6, thi-1, lacY1, galk2, ara-14, xyl-5, mtl-1, proA2, his-4, argE3, rpsL31, tsx-33, sup44, recJ284::Tn10 |
| CAG12156 | MG1655 (E. coli K-12 F$^-$ λ) uvrC279::Tn10 |
| JC8947 | AB1157 (standard E. coli K-12) umcC::Tn5 |
| AG279 | same as JC12166 except recJ$^+$, recF143, fuc::Tn10 |
| JH122 | GW1000 (standard E. coli K12, mcrB4::Tn10, mrr2::Tn5, hsdR2) |
| BB4 | hsdR514, supE44, supP58, lacY1, galK2, galT22, metB1, trpR55, {F'(lacI$^Q$Z M15::Tn10} |
| AG239 | thi, gyrA, supE44, lac$^-$(uncharacterized) Tet$^R$ |
| AG1 | recA, endA1, gyrA96, thi, hsdR17, supE44, relA |
| C600· | supE44, thi-1, leuB6, lacY1, tonA21, mcrA |
| NM621· | recD, hsdR, mcrA, mcrB, supE |
| HB101 | hsdS20, supE44, ara14, galK2, lacY1, proA2, rpsL20, xyl-5, recA13, mcrB |
| TB1· | ara, (lac-proAB), rpsL, 80, lacZ$^\wedge$M15, hsdR |
| DH5α | recA1, endA1, relA1, thi, hsdR17, supE44, gyrA96 |

ER1451 cells were grown at 37° C. to a density of 5×10$^8$ to 1×10$^9$ cells/ml in media containing tryptone, yeast extract, NaCl and agar (LB media) containing 5 mM CaCl$_2$. Cells were harvested by centrifugation and resuspended in 100 mM MgSo$_4$, 5 mM CaCl$_2$ (MC media) media at 37° C. for 15 minutes. Cells were again harvested by centrifugation and resuspended in ⅒ the original volume of MC media. 0.1 ml of the resulting cell suspension was mixed with a P1 phage, containing the genome of E. coli strain CES229, and incubated at 37° C. for 15 minutes. The reaction was terminated by the addition of 0.1 ml of 0.2M sodium citrate. 0.5 ml of LB media was added and cultures grown at 37° C. for an additional 60 minutes. These incubation conditions were found to be sufficient for expression of transduced DNA. Cells (5×10$^6$) were then plated directly onto LB plates containing 15 μg/ml tetracycline. Transductants were screened for the desired phenotype, then plated onto Bochner plates and screened for tetracycline sensitivity. The culture media for this screening procedure contained in final concentration: 10 g/L tryptone, 5 g/L yeast extract, 15 g/L agar, 10 g/L NaCl, 10 g/L NaH$_2$PO$_4$, 2 g/L glucose, 12 mg/L fusaric acid, 0.1 mM ZnCl$_2$, and 50 mg/L of chlortetracycline. Cell colonies demonstrating a rapid rate of growth and sensitivity to tetracycline were identified, recovered and utilized for subsequent transduction as indicated in FIG. 2. ER1451 cells were sequentially transduced with P1 phages containing the genome of E. coli strains CES229, JC12166, CAG12156, JC8947, AG239, AG279, and JH122. As a result of these transductions, the following genetic mutations were assembled into the original ER1451 strain: phoR; sbcC201; recJ; uvrC; umuC; lac*; fuc; recB21; mcrB and mrr. The resulting E. coli strain, AG324, was subjected to F' mating for the purpose of introducing a tetracycline resistant F'episome carrying a lacI$^Q$ZΔM15 cassette for use in blue/white screening. The final E. coli strain constructed has been named SURE™, a trademark of Stratagene Cloning Systems. The genotype of SURE™ is recB, recJ, sbcC201, phoR, uvrC, umuC::Tn5, mcrA, mcrB, mrr, Δ(hsdRMS), endA1, gyrA96, thi, relA1, lac*, supE44, {F'proAB, lacI$^Q$ZΔM15, Tn10}. The SURE™ strain of E. coli was then used to test for stability of various structurally complex DNA sequences.

EXAMPLE 2
Stability of Inverted Repeats

Figure 3:
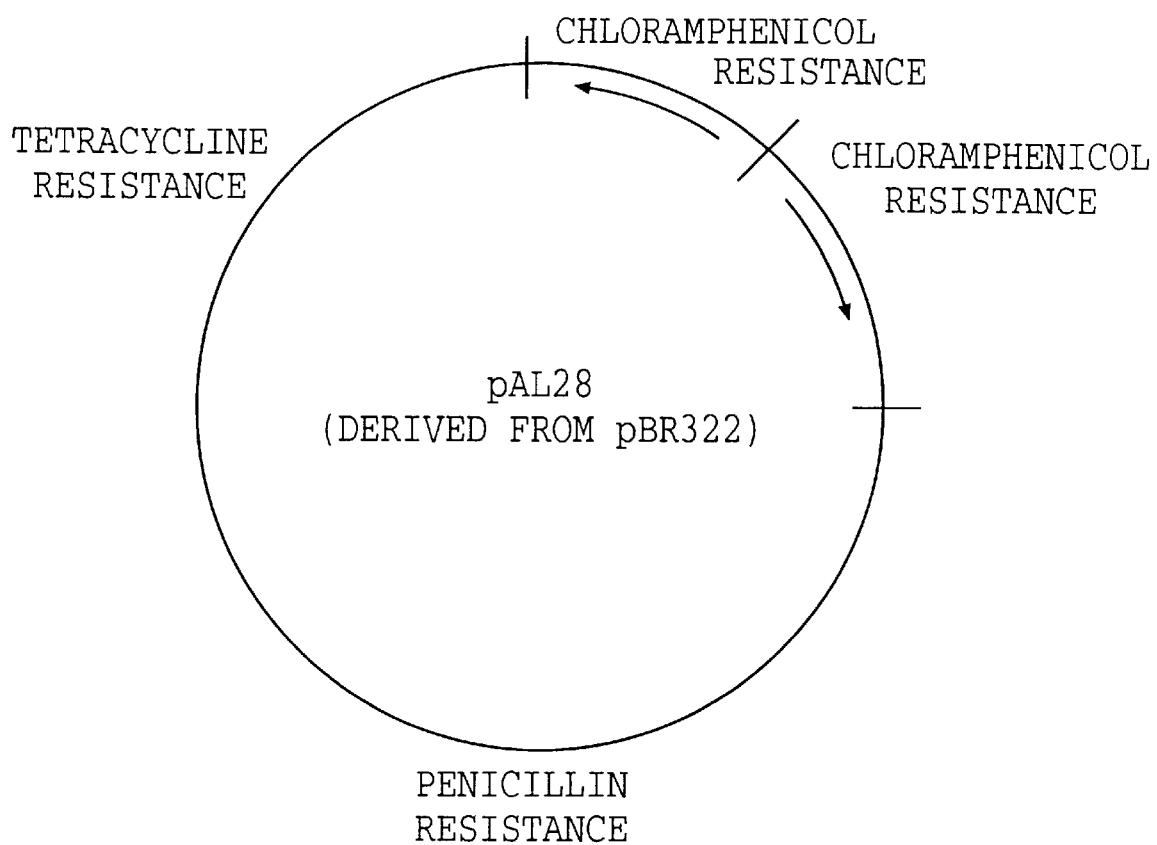
FIG. 3 is a schematic gene map of the inverted repeat tester plasmid, designated pAL28α.

DNA molecules containing an inverted repeat sequence coding for chloramphenicol resistance were created and inserted into modified pBR322 plasmid vectors. A gene map of the inverted repeat tester system, designated plasmid pAL28Δ, is schematically diagramed in FIG. 3. Numerous strains of E. coli, including the SURE™ strain, were transformed with pAL28Δ. Transformants were inoculated in media containing only penicillin and grown for up to 100 generations (with serial dilutions). After every 10 or 20 generations, aliquots of cells were screened on either penicillin containing or chloramphenicol containing plates. Cells in which the inverted repeat chloramphenicol resistant sequences were rearranged lost their chloramphenicol resistance. Percentage of cells generating rearrangement of the tester plasmid could, therefore, be readily determined by monitoring chloramphenicol sensitivity. Results from eight of the strains studied are summarized in Table 2. The genotypes of the strains reported in Table 2 are set forth in Table 1 above.

TABLE #2

STABILITY OF INVERTED REPEATS IN VARIOUS *E. COLI* STRAINS

| Strain | Percentage of cells generating rearranged plasmid per generation[a] |
|---|---|
| AG1 | 15–20 |
| DH5α | 15–20 |
| C600 | 20–25 |
| NM621 | 20–25 |
| HB101 | 15–20 |
| TB1 | 20–25 |
| DL538 | 20–25 |
| SURE ™ | 0.8–1.2 |

[a]Percent rearrangement calculated from the number of cells maintaining the inverted repeat tester plasmid in its unrearranged configuration (chloramphenicol resistant) divided by the total number of plasmid-containing cells.

It is evident from the data in Table 1 that only the SURE™ *E. coli* strain markedly reduced DNA rearrangement. The internal environment of the SURE™ strain, therefore, provides a stabilizing influence on inverted repeat DNA sequences. Note that each of the *E. coli* strains tested contained at least some of the mutations found in the SURE™ strain. It is important to note here that even though some strains (i.e., DH5α) contained mutations in different metabolic pathways (homologous recombination, restriction pathway and endonuclease), such combined mutations were not effective in diminishing the rate of rearrangement. Because the presence of these individual mutations in other strains did not prevent rearrangement of the inverted repeat DNA sequence, it appears as though it is the combination of repair and recombination mutations in SURE™ that is responsible for increased stability.

EXAMPLE 3

Stability of Z-DNA

Figure 4:
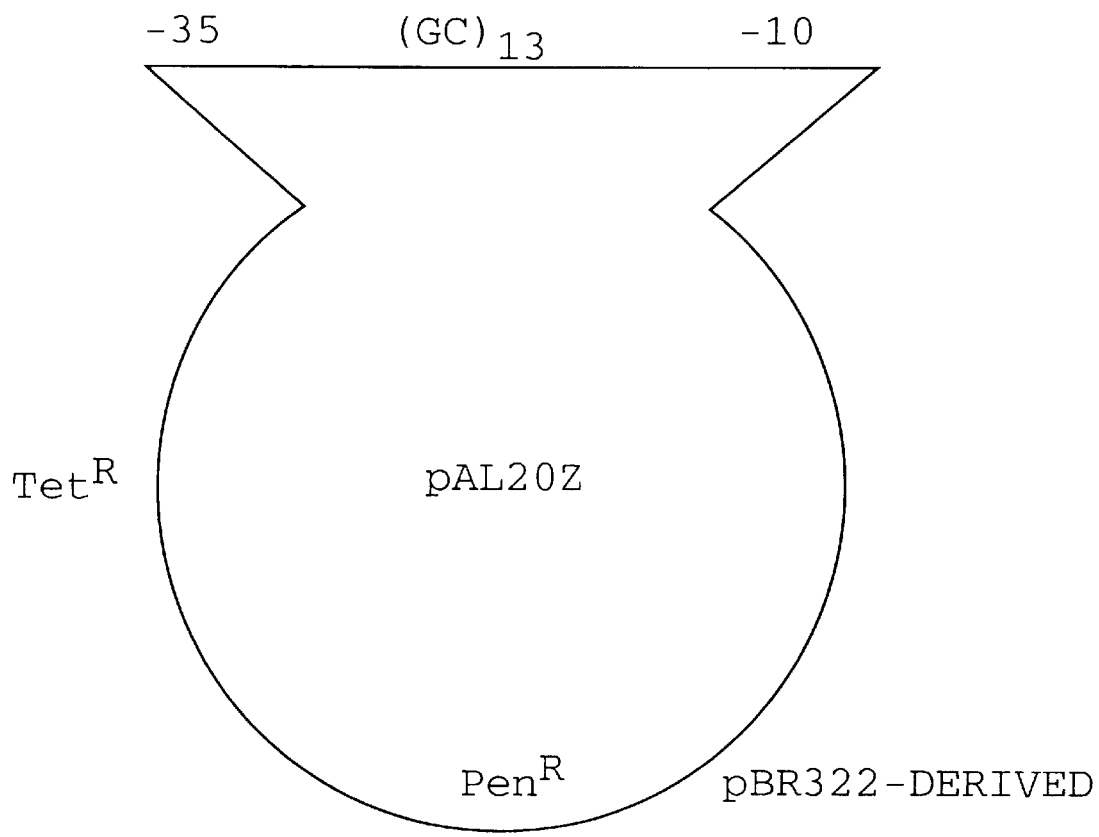
FIG. 4 is a schematic gene map of the Z-DNA tester plasmid system, designated pAL20Z.

DNA molecules were created which contained alternating purine and pyrimidine residues capable of forming Z-DNA. These Z-DNA containing sequences were inserted into a modified pBR322 plasmid designated pAL20Z (see FIG. 4). A sequence of 26 alternating purine-pyrimidine residues (GC) were inserted into and blocked expression of the promoter region for chloramphenicol resistance. Because of the absence of a promoter in the intact plasmid, host cells containing pAL20Z demonstrate chloramphenicol sensitivity. Deletion of the repeating sequences results in reconstitution of the promoter and, therefore, expression of chloramphenicol resistance. A variety of *E. coli* host strains were transformed with pAL20Z. Transformants were inoculated into media containing penicillin and grown for up to 200 generations (with serial dilutions). After every 20 generations, $10^6$ cells were plated onto media containing chloramphenicol (50 μg/ml). The percentage of cells demonstrating chloramphenicol resistance was taken as a direct reflection of the percent of cells rearranging the tester plasmid. The results from transformation of seven of these *E. coli* strains, including the SURE™ strain, are shown below in Table 3. The genotypes of these *E. coli* strains can be found in Table 1.

TABLE #3

STABILITY OF Z-DNA IN VARIOUS *E. COLI* STRAINS

| Strain | Percentage of cells generating rearranged plasmids per 25 generations[a] |
|---|---|
| AG1 | 15 |
| DH5α | 15 |
| C600· | 10 |
| NM621· | 20 |
| HB101 | 15 |
| TB1· | 10 |
| SURE ™ strain | <0.1 |

[a]Percent Z-DNA rearrangement calculated by determining the percentage of chloramphenicol resistant cells (indicative of a specific Z-DNA rearrangement) within a population after 25 generations.

It is evident from these data that the SURE™ *E. coli* strain significantly and markedly reduced the amount of DNA rearrangement. The SURE™ strain, therefore, provides a stabilizing environment for Z-DNA. Taken together, the data from Examples 2 and 3 demonstrate that a cloning host organism can be engineered and constructed such that it provides a stabilizing environment for complex DNA molecules capable of forming secondary and tertiary structures. Furthermore, the data demonstrate that this host organism is effective in inhibiting rearrangements of DNA molecules capable of forming a variety of such secondary and tertiary structures.

A novel strain of bacteria has been engineered by combining a number of mutations which significantly reduce the rate of both homologous and non-homologous recombination within segments of cloned foreign DNA. Non-bacterial DNA, particularly from eucaryotic sources, frequently contain sequences capable of forming secondary and tertiary structures such as cruciforms (due to presence of inverted repeats) or Z-DNA (found in alternating purine-pyrimidine stretches). These structures are highly recombinogenic in standard bacterial cloning hosts which are incapable of carrying out homologous recombination. Mutations which eliminate certain repair pathways responsible for excision of or replication past DNA lesions greatly stabilize these unusual structures. By engineering mutations which eliminate these pathways into a host strain deficient in homologous recombination, a novel host that is suitable for cloning foreign DNA has been constructed.

I claim:

1. A culture of an *E. coli* bacterium obtained from American Type Culture Collection deposit number 55695 having a genome comprising mutations in at least one gene in RecF pathway recombination system and in at least one gene in the SOS DNA repair system, wherein the mutated gene in the SOS DNA repair system is not the same as any gene in the RecF pathway recombination system, such that the bacterium contains cloned eukaryotic DNA containing a nucleotide sequence which forms an inverted repeat or a Z-DNA structure without rearrangement in said cloned eukaryotic DNA.

2. The culture of claim 1, wherein the bacterium has at least one mutation selected from the group consisting of recJ, recA and recB.

3. The culture of claim 1, wherein the bacterium further comprises a mutation in a gene in the host endonuclease system.

4. The culture of claim 1, wherein the bacterium further comprises a mutation in a gene in the host restriction system.

5. The culture of claim 4, wherein the mutation in the gene in the host restriction system is selected from the group consisting of hsd, mcr, and mrr.

6. The culture of claim 5, wherein the *E. coli* genome comprises mutations recB, recJ, sbcC, phoR, uvrC, umuC, mcrA, mcrB, mrr, hsdRMS, endA1, and gyrA96.

7. The culture of claim 6, wherein said *E. coli* further comprises a lac mutation.

8. The culture of claim 2, wherein the *E. coli* genome comprises mutations recB, recJ, sbcC, phoR, uvrC, and umuC.

9. A recombinant genetic library of eukaryotic DNA which contains segments which form rearrangeable secondary and/or tertiary structures maintained in the bacterial culture according to claim 1.

10. A recombinant genetic library of eukaryotic DNA which contains segments which form rearrangeable secondary and/or tertiary structures maintained in the bacterial culture according to claim 2.

11. A recombinant genetic library of eukaryotic DNA which contains segments which form rearrangeable secondary and/or tertiary structures maintained in the bacterial culture according to claim 3.

12. A bacterium isolated from the culture according to claim 1, wherein the bacterium contains an artificial genetic construction.

13. A bacterium isolated from the culture according to claim 2, wherein the bacterium contains an artificial genetic construction.

14. A bacterium isolated from the culture according to claim 3, wherein the bacterium contains an artificial genetic construction.

15. A method of constructing an *E. coli* bacterium obtained from American Type Culture Collection deposit number 55695 which contains cloned eukaryotic DNA containing a nucleotide sequence which forms an inverted repeat or a Z-DNA structure without rearrangement in said cloned eukaryotic DNA, which comprises:

(a) transforming a bacterial cell with DNA having at least one mutation in the RecF pathway recombination system and with DNA having at least one mutation in the SOS DNA repair system, wherein the mutated gene in the SOS DNA repair system is not the same as any gene in the RecF pathway recombination system;

(b) testing the transformed bacterial host of step (a) by further transforming the host with DNA having an inverted repeat or a Z-DNA structure and detecting the stability of an inverted repeat or a Z-DNA structure.

16. The library of claim 9, wherein said library comprises eukaryotic DNA selected from the group consisting of genomic DNA and cDNA.

17. The library of claim 10, wherein said library comprises eukaryotic DNA selected from the group consisting of genomic DNA and cDNA.

18. The library of claim 11, wherein said library comprises eukaryotic DNA selected from the group consisting of genomic DNA and cDNA.

19. The library of claim 16, wherein said eukaryotic DNA is present in a vector selected from the group consisting of a plasmid, a phage, and a cosmid.

20. The library of claim 17, wherein said eukaryotic DNA is present in a vector selected from the group consisting of a plasmid, a phage, and a cosmid.

21. The library of claim 18, wherein said eukaryotic DNA is present in a vector selected from the group consisting of a plasmid, a phage, and a cosmid.

22. An *E. coli* chromosome obtained from American Type Culture Collection Deposit number 55695 comprising mutations in at least one gene in the RecF pathway recombination system and in at least one gene in the SOS DNA repair system, wherein the mutated gene in the SOS DNA repair system is not the same as any gene in the RecF pathway recombination system.

23. The *E. coli* chromosome of claim 22, comprising the mutations recB, recJ, sbcC, phoR, uvrC, umuC, mcrA, mcrB, mrr, hsdRMS, endA1, and gyrA96.

24. The *E. coli* chromosome of claim 23, further comprising a lac mutation.

* * * * *